United States Patent
Cox et al.

(10) Patent No.: US 7,510,704 B2
(45) Date of Patent: Mar. 31, 2009

(54) COSMETIC COMPOSITIONS

(75) Inventors: Diana Sheila Cox, Bedford (GB);
Alexander Gordon James, Bedford (GB); David Taylor, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 321 days.

(21) Appl. No.: 10/481,346

(22) PCT Filed: Jun. 10, 2002

(86) PCT No.: PCT/EP02/06376

§ 371 (c)(1),
(2), (4) Date: Dec. 17, 2003

(87) PCT Pub. No.: WO03/000218

PCT Pub. Date: Jan. 3, 2003

(65) Prior Publication Data

US 2004/0180012 A1 Sep. 16, 2004

(30) Foreign Application Priority Data

Jun. 22, 2001 (GB) ................................ 0115344.4

(51) Int. Cl.
*A61K 8/00* (2006.01)
*A61K 8/02* (2006.01)
*A61K 31/075* (2006.01)

(52) U.S. Cl. ........................ 424/65; 424/401; 514/718

(58) Field of Classification Search .................. 424/401
See application file for complete search history.

(56) References Cited

U.S. PATENT DOCUMENTS

| 3,792,068 | A | | 2/1974 | Luedders ................. 260/429.3 |
| 4,356,190 | A | | 10/1982 | Kraskin ....................... 424/319 |
| 5,002,762 | A | * | 3/1991 | Bolich, Jr. ................. 424/70.12 |
| 5,067,897 | A | * | 11/1991 | Tuneberg ........................ 433/8 |
| 5,176,903 | A | * | 1/1993 | Goldberg et al. .............. 424/66 |
| 5,770,185 | A | | 6/1998 | Wachter et al. ................ 424/65 |
| 6,045,784 | A | * | 4/2000 | Ruebusch et al. ............. 424/65 |
| 6,153,226 | A | * | 11/2000 | Vachy et al. ................. 424/539 |
| 6,171,582 | B1 | * | 1/2001 | Casey et al. ................... 424/65 |
| 6,325,565 | B1 | * | 12/2001 | Girardot et al. ............. 401/266 |
| 6,362,378 | B1 | * | 3/2002 | Jacquot et al. .............. 568/644 |
| 6,576,247 | B1 | * | 6/2003 | Ikemoto et al. ............. 424/401 |

FOREIGN PATENT DOCUMENTS

| DE | 43 43 264 | | 6/1995 |
| DE | 43 43 265 | | 6/1995 |
| DE | 293 958 | | 9/2001 |
| EP | 545 556 | | 7/1997 |
| JP | 63 292962 | | 11/1988 |
| JP | 03275392 | * | 5/1993 |
| JP | 09-111285 | * | 4/1997 |
| JP | 2000096078 | * | 9/2000 |
| WO | 00/01353 | | 1/2000 |
| WO | 00/01356 | | 1/2000 |

OTHER PUBLICATIONS

PCT International Search Report in a PCT application PCT/EP 02/06376.
Derwent Abstract of JP 59 029619—published Feb. 16, 1984.
Derwent Abstract of JP 05 117972—published May 14, 1993.
Derwent Abstract of JP 2000 096078—published Apr. 4, 2000.
Derwent Abstract of JP 2000 191520—published Jul. 11, 2000.
Derwent Abstract of JP 60 023309—published Feb. 5, 1985.
Derwent Abstract of JP 11 116460—published Apr. 27, 1999.
Derwent Abstract of DD 293 958—published Sep. 19, 1991.
Derwent Abstract of DE 43 43 265—published Jun. 22, 1995.
Derwent Abstract of JP 63-292962—published Nov. 30, 1988.

* cited by examiner

*Primary Examiner*—M P Woodward
*Assistant Examiner*—Bethany Barham
(74) *Attorney, Agent, or Firm*—Karen E. Klumas

(57) ABSTRACT

This invention concerns cosmetic compositions and methods involving 4-hydroxy-3-methoxybenzyl alcohol as an active ingredient. This material is shown to be an extremely effective sub-lethal inhibitor of the metabolism of selected corynebacteria and to give significant deodorancy benefits.

11 Claims, No Drawings

COSMETIC COMPOSITIONS

FIELD OF INVENTION

This invention relates to cosmetic compositions for reducing or preventing body malodour. In particular, it relates to cosmetic compositions comprising a highly effective, sub-lethal inhibitor of selected *corynebacteria*.

BACKGROUND

It is well known that freshly secreted sweat is sterile and that body malodour is the result of biotransformation of the sweat by microorganisms living on the surface of the skin to produce volatile odoriferous compounds.

There are three types of material routinely used to combat body malodour: perfumes, antiperspirants and deodorants.

Perfumes typically work by simply masking body malodour.

Antiperspirants work by blocking the sweat glands, thereby reducing perspiration. However, even the best cosmetically acceptable antiperspirants rarely reduce sweat production by more than 50%.

Typical deodorants work by reducing the population of micro-organisms living on the surface of the skin, thereby reducing the extent of sweat biotransformation referred to above. Typical deodorants include ethanol and triclosan (2,4,4'-trichloro,2'-hydroxy-diphenyl ether). However, the skin is host to a number of species of microorganism, some of which are beneficial. The use of typical deodorants results in the killing of these beneficial species, in addition to the odour-producing species. This is an undesirable side effect of such deodorants.

The present invention concerns malodour reduction via the sub-lethal inhibition of certain *corynebacteria*, as described in WO 00/01356 (Quest International BV) and WO 00/01353 (Unilever), the latter of which is incorporated herein by reference. These prior publications disclose the sub-lethal inhibition of *corynebacteria* that are capable of catabolising fatty acids. Many materials are described as having this effect; however, the highly effective compositions of the present application are not disclosed.

WO 00/01353 (Unilever) uses the term "*corynebacteria A*" to mean *corynebacteria* that are able to catabolise fatty acids; this term is used with the same meaning in the present application. Such bacteria contribute strongly to the formation of body malodour, in particular axillary malodour. For many males, malodour formation is largely caused by *corynebacteria A*.

The deodorants presently available on the market tend to be insufficiently effective or substantially reduce the numbers of all bacteria on the skin indiscriminately. The present invention offers the opportunity to provide cosmetic compositions, which, for many females, will substantially reduce malodour formation while inactivating only a minor portion of the skin microflora. For many males, malodour formation can be substantially reduced or even largely eliminated while inactivating only one subgroup of the skin microflora, the *corynebacteria A*.

Furthermore, the specific active ingredient disclosed in the present application is effective at particularly low concentrations.

Other publications in the prior art describe alternative deodorancy methods that do not indiscriminately kill the skin microflora.

DD 29 39 58 (Medezinische Fakultaet [Charité] der Humboldt Universitaet zu Berlin) describes the use of lipoxygenase inhibitors to act biochemically to reduce sweat production or to inhibit, to various degrees, the action of skin bacteria or their enzymes on the decomposition of sweat to form unpleasant-smelling substances.

DE 43 43 265 (Henkel) describes deodorant compositions comprising saturated dioic acid (C3-C10) esters. The active inhibits a sweat decomposing esterase and the compositions are said to not disturb the skin's natural microflora.

DE 43 43 264 (Henkel) describes the use of lipid-soluble partial esters of hydroxy carboxylic acids in deodorant compositions.

U.S. Pat. No. 4,356,190 (Personal Products Co.) describes a deodorancy method utilising selected aminopolycarboxylic acids that function whilst maintaining the viability of *corynebacteria*.

New deodorants containing p-hydroxybenzaldehyde or p-hydroxybenzyl alcohol are described in JP 63,292,962 (Matsushita Electric Works Ltd.).

SUMMARY OF THE INVENTION

According to a first aspect of the invention, there is provided a cosmetic composition comprising 4-hydroxy-3-methoxybenzyl alcohol.

According to a second aspect of the invention, there is provided a cosmetic method of obtaining a deodorancy benefit comprising the topical administration of 4-hydroxy-3-methoxybenzyl alcohol.

DETAILED DESCRIPTION 4-hydroxy-3-methoxybenzyl alcohol, the active ingredient utilised in the present invention, is capable of inhibiting fatty acid catabolism by *corynebacteria A* at a concentration below that which would lead to the death of said *corynebacteria A*. The active ingredient leads to a deodorancy benefit without significant harm to the skin's natural microflora. In addition, the active ingredient is effective at particularly low concentrations, being able to reduce the fatty acid catabolism of *corynebacteria A* by greater than 50% at a concentration of 0.5 mg/ml or less.

The aforementioned inhibitory effect may be described as sub-lethal, in that the effect is obtained at a concentration below that which would lead to the death of the *corynebacteria A*. The effect may be further defined as a significant inhibition of fatty acid catabolism, for example greater than 50% inhibition of pentadecanoic acid utilisation, without a concomitant reduction in cell viability ($\leq 1$ $\log_{10}$ CFU/ml reduction) of the *corynebacteria A*. The active ingredient is able to produce this effect at a concentration of 0.25 mg/ml or less.

The active ingredient may be employed in any cosmetic composition. A particularly useful application is in deodorant compositions, particularly those used on the human body, and especially those used for treatment of underarm and/or foot malodour.

Compositions according to the invention comprise an effective total concentration of active ingredient; that is to say, a concentration sufficient to inhibit the catabolism of fatty acids by *corynebacteria A* on normal use of the composition. Typical concentrations range from 0.001 to 10%, preferably from 0.01 to 5%, and especially from 0.2 to 2% by weight of the composition.

In one aspect of the invention, it is desirable that the compositions of the invention do not comprise significant amounts of additional anti-microbial agents that cause lethal inhibition of *corynebacteria A*. It is desirable that the total concentration of such anti-microbial agents is less than the total concentration of active ingredients according to the invention; indeed, it is preferred that the total concentration of such anti-microbial agents is less than half, and especially less than one tenth, of this amount.

Active ingredients that cause lethal inhibition of *corynebacteria A* may be defined as those causing $\geq 1 \log_{10}$ CFU/ml reduction in cell viability when tested by methods common in the art, for example the method described in Example 1 of the present specification (vide infra).

Cosmetic compositions according to the invention may take any of a variety of forms. Typical forms include aerosols, sticks, soft solids, creams, gels, roll-ons, pump sprays, squeeze sprays, and compositions for application to deodorant wipes. All of the above forms are particularly applicable forms of deodorant composition.

Cosmetic compositions according to the invention comprise one or more components in addition to the active ingredient. A commonly employed additional component is a carrier material. Such materials serve to aid the delivery of the active ingredient to the desired target. Preferred carrier materials are liquids at ambient temperature and atmospheric pressure. Hydrophobic liquids suitable for use include liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, and aliphatic or aromatic ester oils (e.g. isopropyl myristate, lauryl myristate, isopropyl palmitate, diisopropyl sebecate, diisopropyl adipate, or $C_8$ to $C_{18}$ alkyl benzoates).

Hydrophilic liquid carrier materials, for example water, may also be employed.

Particularly preferred liquid carrier materials comprise organic solvents. Preferred organic solvents have a melting point of less than 10° C., preferably less than 5° C.; this can benefit both low temperature storage stability and ease of manufacture. A class of preferred organic solvents are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol propylene glycol, butylene glycol, ethanol, propanol, isopropanol, and industrial methylated spirits. The most preferred organic solvents are aliphatic alcohols, in particular those having 2 to 3 carbon atoms, especially ethanol and isopropanol.

Mixtures of carrier materials may also be used. The total amount of carrier material employed is preferably from 1 to 99%, more preferably from 10% to 98%, and most preferably from 50% to 97% by weight of the composition, excluding any volatile propellant that might also be present.

A variety of other materials may also be employed in the compositions of the invention. In certain aspects of the invention, an additional deodorant active may be desirable. This might be a perfume, an antiperspirant active, or an anti-microbial active.

Perfumes, when employed, may be conventional perfumes, such as perfume oils, and/or so-called deo-perfumes, as described in EP 545,556 and other publications. Levels of incorporation are preferably up to 4% by weight, particularly from 0.1% to 2% by weight, and especially from 0.7% to 1.7% by weight of the composition.

Compositions according to the invention that additionally comprise an antiperspirant active are particularly preferred.

Typical antiperspirant actives include astringent active salts, in particular, aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates. Preferred levels of incorporation are from 0.5% to 60%, particularly from 5% to 30% or 40% and especially from 5% or 10% to 30% or 35% by weight of the composition of which it is a part. In non-aqueous formulations, the above weight percentages exclude any water of hydration bound to the antiperspirant salt. Especially preferred aluminium halohydrate salts, known as activated aluminium chlorohydrates, are described in EP 6,739 (Unilever PLC and NV). Zirconium aluminium chlorohydrate actives are also preferred materials, as are the so-called ZAG (zirconium-aluminium-glycine) complexes, for example those disclosed in U.S. Pat. No. 3,792,068 (Procter and Gamble Co.).

Typical anti-microbial actives include quaternary ammonium compounds (like cetyltrimethylammonium salts), chlorhexidine and salts thereof; diglycerol monocaprate, diglycerol monolaurate, glycerol monolaurate, polyhexamethylene biguanide salts (also known as polyaminopropyl biguanide salts—an example being Cosmocil CQ available from Zeneca PLC), 2,4,4'-trichloro, 2'-hydroxy-diphenyl ether (triclosan), and 3,7,11-trimethyldodeca-2,6,10-trienol (farnesol). Typical levels of incorporation are from 0.01% to 1%, in particular from 0.03% to 0.5%, or especially from 0.05% to 0.3% by weight of the composition.

Particularly preferred additional deodorant actives are agents that are capable of sub-lethal inhibition of *corynebacteria A*, in particular, sub-lethal inhibition of fatty acid catabolism by *corynebacteria A*. The effect may be further defined as a significant inhibition of fatty acid catabolism, for example greater than 50% inhibition of pentadecanoic acid utilisation, without a concomitant reduction in cell viability ($\leq 1 \log_{10}$ CFU/ml reduction) of the *corynebacteria A*. Such agents may be used in concentrations ranging from 0.001 to 10%, in particular from 0.05 to 5%, and especially from 0.3 to 3% by weight of the composition. Examples of such agents are described in WO 00/01356 (Quest International BV) and WO 00/01353 (Unilever). Other examples are the chelating agents described in U.S. Pat. No. 4,356,190 (Personal Products Co.) and/or our co-pending application PCT/EP01/00118 (Unilever), particularly those chelating agents having an iron (III) binding constant of greater than $10^{26}$. DTPA (diethylenetriaminepentaacetic acid) and salts thereof are especially preferred.

Structurants and emulsifiers are further additional components of the compositions of the invention that are highly desirable in certain product forms. Structurants, when employed, are preferably present at from 1% to 30% by weight of the composition, whilst emulsifiers are preferably present at from 0.1% to 10% by weight of the composition. Suitable structurants include cellulosic thickeners such as hydroxy propyl cellulose and hydroxy ethyl cellulose, and dibenzylidene sorbitol. Emulsion pump sprays, roll-ons, creams, and gel compositions according to the invention can be formed using a range of oils, waxes, and emulsifiers. Suitable emulsifiers include steareth-2, steareth-20, steareth-21, ceteareth-20, glyceryl stearate, cetyl alcohol, cetearyl alcohol, PEG-20 stearate, and dimethicone copolyol. Suspension aerosols, roll-ons, sticks, and creams require structurants to slow sedimentation (in fluid compositions) and to give the desired product consistency to non-fluid compositions. Suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Some of the above materials also function as suspending agents in certain compositions.

Further emulsifiers desirable in certain compositions of the invention are perfume solubilisers and wash-off agents. Examples of the former include PEG-hydrogenated castor oil, available from BASP in the Cremaphor RH and CO ranges, preferably present at up to 1.5% by weight, more preferably 0.3 to 0.7% by weight. Examples of the latter include poly(oxyethylene) ethers.

Sensory modifiers are further desirable components in certain compositions of the invention. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (e.g. Aerosil 200), polyethylene (eg. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Cosmetic compositions that are aerosols generally also comprise a volatile propellant. The propellant may be selected from liquified hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

Other additional components that may also be included are colourants and preservatives, for example $C_1$-$C_3$ alkyl parabens.

EXAMPLES

This experiment uses the methods of WO 00/01353 to illustrate the much greater efficacy of 4-hydroxy-3-methoxybenzyl alcohol at inhibiting fatty acid catabolism by *corynebacteria A*, when compared with analogous materials previously disclosed in the aforementioned publication. Data illustrating the sub-lethal aspect of the inhibition are also presented.

An in vitro model system, reproducing fatty acid catabolism by axillary bacteria, was used. To each of several 250 ml baffled shake flasks was added 30 ml semi-synthetic medium (see below), supplemented with fatty acid substrate (2.0 mg/ml pentadecanoic acid) and non-fatty acid substrate (0.5 mg/ml glucose). To each flask (other than the control) was also added one of the indicated test materials, as a 10% (w/v) emulsion in semi-synthetic medium, supplemented with Gum Arabic (5.0 mg/ml). (Emulsions were formed by ultra-homogenisation at 24,000 rpm for about 1 min.) Each of the flasks was inoculated with fresh bacterial biomass (*Corynebacterium A* sp. NCIMB 40928), pre-grown for 24 h in TSBT (see below), to give starting optical densities ($A_{590}$) of 1.0-2.0. Following inoculation, the flasks were incubated aerobically at 35° C., with agitation (130 rpm), for 24 hours. After this time, culture viability and remaining fatty acid were determined by methodology as described in WO 99/01359.

Composition of semi-synthetic medium in g/l: $KH_2PO_4$ (1.6), $(NH_4)_2HPO_4$ (5.0), $Na_2SO_4$ (0.38), yeast nitrogen base (3.35) (Difco), yeast extract (0.5) (Beta Lab), Tween 80™ (0.2), Triton X-100™ (0.2), and $MgCl_2.6H_2O$ (0.5).

Composition of TSBT (Tween-supplemented Tryptone soya broth) in g/l: Tryptone soya broth (30.0) (Merck), yeast extract (10.0) (Beta Lab), and Tween 80™ (1.0).

Table 1 illustrates the effects of the indicated actives upon *Corynebacterium A* sp. NCIMB 40928 in terms of culture viability and fatty acid utilisation. Various concentrations of active were investigated. It will be noted that for each of the Examples, culture viability was not substantially affected.

TABLE 1

Effect of Actives upon *Corynebacterium* A sp. NCIMB 40928 (Comparative examples are indicated by letter codes)

| Example | Conc. (g/l) | Viability ($\log_{10}$CFU/ml) | Fatty acid utilisation (%) |
|---|---|---|---|
| 1. | 0 | 9.12 | 100 |
| 4-hydroxy-3-methoxybenzyl alcohol | 0.1 | 8.91 | 65 |
| | 0.25 | 8.88 | 40 |
| | 0.5 | 8.28 | 20 |
| A. | 0 | 8.17 | 100 |
| 4-hydroxybenzyl alcohol | 0.1 | 8.69 | 100 |
| | 0.25 | 8.85 | 97 |
| | 0.5 | 8.17 | 21 |
| B. | 0 | 8.98 | 100 |
| 3-hydroxy-4-methoxybenzyl alcohol | 1.0 | 8.90 | 99 |
| | 5.0 | 8.99 | 86 |
| | 10.0 | 8.62 | 29 |
| C. | 0 | 8.75 | 100 |
| 4-hydroxy-3-methoxyphenethyl alcohol | 1.0 | 8.80 | 99 |
| | 5.0 | 8.60 | 59 |
| | 10.0 | 8.09 | 26 |

These data illustrate that the active of the invention is an effective inhibitor of fatty acid catabolism by *corynebacteria A* at a considerably lower concentration than analogous materials disclosed in the prior art.

Examples 3 to 11

The following are typical compositions according to the invention and were prepared by methods common in the art. Examples 3 to 8 are aerosol compositions, Example 9 is a pump spray composition, Example 10 is an antiperspirant stick composition, and Example 11 is a roll-on composition.

TABLE 2

Composition of Examples 3 to 8 (amounts given in the Tables are percentages by weight)

| | Example: | | | | | |
|---|---|---|---|---|---|---|
| | 3 | 4 | 5 | 6 | 7 | 8 |
| CAP 40[1] | 92 | 85 | 35 | 84.96 | 85 | 35 |
| Ethanol (96%) | 0 | 0 | 62.17 | 0 | 0 | 61.16 |
| DC 245[2] | 6.2 | 6.9 | 0 | 6.4 | 6.5 | 0 |

TABLE 2-continued

Composition of Examples 3 to 8
(amounts given in the Tables are percentages by weight)

| | Example: | | | | | |
|---|---|---|---|---|---|---|
| | 3 | 4 | 5 | 6 | 7 | 8 |
| AACH[3] | | 5 | 0 | 5 | 5 | 0 |
| 4-hydroxy-3-methoxybenzyl alcohol | 1.0 | 2.0 | 1.0 | 1.0 | 1.0 | 1.0 |
| Bentone 38[4] | 0.6 | 0.5 | 0 | 0.5 | 0.5 | 0 |
| DTPA[5] | 0 | 0 | 0 | 1.0 | 0 | 0 |
| Cosmocil stearate[6] | 0 | 0 | 0 | 0.04 | 0 | 0 |
| Irgasan DP-300[7] | 0 | 0 | 0 | 0 | 0 | 0.01 |
| Ferulic acid[8] | 0 | 0 | 0 | 0 | 1.0 | 1.0 |
| Perfume | 0 | 0.6 | 1.5 | 1.0 | 1.0 | 1.5 |
| Isopropyl myristate | 0 | 0 | 0.33 | 0 | 0 | 0.33 |
| Propylene carbonate | 0.2 | 0 | 0 | 0 | 0 | 0 |

[1]Mixture of butane, isobutane and propane, ex Calor.
[2]Cyclomethicone, ex Dow Corning.
[3]Activated aluminium chlorohydrate, grade A296, ex Giulini.
[4]Quaternium-18 hectorite, ex Rheox.
[5]Diethylenetriaminepentaacetic acid, sieved to <63 µm.
[6]Polyhexamethylene biguanide salt, ex Zeneca.
[7]Triclosan, ex Ciba-Geigy.
[8]4-Hydroxy-3-methoxycinnamic acid, a deodorant active as disclosed in WO 00/01359 (Unilever).

Example 4 was found to have a significantly better deodorancy performance than a control composition having the 4-hydroxy-3-methoxybenzyl alcohol replaced by DC 245. A similar benefit was obtained with an analogous composition comprising only 1% (w/w) 4-hydroxy-3-methoxybenzyl alcohol.

TABLE 3

Composition of Examples 9, 10, and 11

| | Example: | | |
|---|---|---|---|
| | 9 | 10 | 11 |
| Ethanol | 59.4 | 0 | 70 |
| Water | 39.6 | 0 | 27.85 |
| 4-hydroxy-3-methoxybenzyl alcohol | 1.0 | 1.0 | 1.0 |
| Cremaphor RH40[1] | 0 | 0 | 0.5 |
| Klucel M[2] | 0 | 0 | 0.65 |
| AAZG[3] | 0 | 25 | 0 |
| DC 245 | 0 | 50.8 | 0 |
| Stearyl alcohol | 0 | 14 | 0 |
| Superfino talc | 0 | 3.2 | 0 |
| PEG-8 distearate | 0 | 1 | 0 |
| Castorwax MP80 | 0 | 4 | 0 |
| Perfume | 0 | 1 | 0 |

[1]PEG-hydrogenated castor oil, ex BASF.
[2]Hydroxypropylcellulose, ex Aqualon.
[3]Aluminium zirconium tetrachlorohydrex-glycine, Q5-7167, ex Summit.

Example 10 was found to have a significantly better deodorancy performance than a control composition having the 4-hydroxy-3-methoxybenzyl alcohol replaced by DC 245. A similar benefit was obtained with an analogous composition comprising 2% (w/w) 4-hydroxy-3-methoxybenzyl alcohol and 49.8% (w/w) DC 245.

Examples 12 to 17

Tables 4 to 9 illustrate other compositions according to the invention that may be prepared by methods common in the art.

TABLE 4

Composition of Examples 12.1 to 12.6 (aerosol compositions)

| | Example: | | | | | |
|---|---|---|---|---|---|---|
| | 12.1 | 12.2 | 12.3 | 12.4 | 12.5 | 12.6 |
| Cyclomethicone (DC 245) | 3.47 | 11.8 | 14.4 | 3.55 | 4.1 | 5.2 |
| Ethanol | | | 20 | | | |
| Isopropyl palmitate | | | 10.3 | | 8.5 | |
| Isopropyl myristate | | | | | | 0.31 |
| PPG-14 butyl ether | 9.7 | 0.7 | | | | 9.1 |
| Octyldodecanol | | | 0.25 | | | |
| Polydecene | | | | | | 0.3 |
| Dibutyl phthalate | | | | | 4.5 | |
| Bentone 38 (ex Rheox) | 1 | 1 | 1.5 | 1 | 0.95 | 0.7 |
| Propylene carbonate | | | | | 0.15 | |
| Methylpropanolamine | | | | | | 0.08 |
| Silicone gum (Q2-1401) | | | | 0.2 | | |
| AACH | | | 10 | | 4 | |
| Milled AACH | 10 | | | | | 2 |
| Aluminium chlorohydrate | | | | 9.2 | 9.3 | |
| Silica | | 0.1 | | | | 0.01 |
| Talc | | | | 3 | | |
| Micronised polyethylene | | | | | 9.3 | |
| Perfume | 0.5 | 0.7 | 0.7 | 0.7 | | 1 |
| Allantoin | | | | | 1.5 | |
| Palmitoyl ethanolamide | 0.3 | 0.3 | 0.3 | 0.3 | 0.3 | 0.3 |
| 4-hydroxy-3-methoxybenzyl alcohol | 0.03 | 0.15 | 0.6 | 0.25 | 1.4 | 1 |
| n-Pentane | | | | 20 | | |
| C3/C4 hydrocarbons | 75 | 75 | 40 | 70 | 60 | 80 |

TABLE 5

Composition of Examples 13.1 to 13.9 (lotion compositions)

| | Example: | | | | | | | | |
|---|---|---|---|---|---|---|---|---|---|
| | 13.1 | 13.2 | 13.3 | 13.4 | 13.5 | 13.6 | 13.7 | 13.8 | 13.9 |
| Ethanol | | 30 | | 60 | | | | 28 | |
| Isopropanol | 30 | | 30 | | 30 | 60 | 30 | | |

TABLE 5-continued

Composition of Examples 13.1 to 13.9 (lotion compositions)

| | Example: | | | | | | | | |
|---|---|---|---|---|---|---|---|---|---|
| | 13.1 | 13.2 | 13.3 | 13.4 | 13.5 | 13.6 | 13.7 | 13.8 | 13.9 |
| Hydroxypropyl-cellulose | 0.7 | 0.7 | 0.7 | 0.7 | 0.7 | 0.7 | 0.7 | 0.7 | |
| Aluminium chlorohydrate | | 4 | 4 | | | | 20 | | |
| ZACH | | | | | | | | 20 | |
| AAZG | | | | | | | | | 18 |
| Cosmocil CQ | | | | 0.2 | 0.2 | | | | |
| Triclosan | | | | | | 0.1 | | | |
| Suspending Agent | | | | | | | | | 3 |
| Propylene Carbonate | | | | | | | | | 1 |
| Talc | | | | | | | | | 6 |
| 4-hydroxy-3-methoxybenzyl alcohol | 0.2 | 0.4 | 0.6 | 0.8 | 1 | 2 | 3 | 4 | 5 |
| Water + minors | 69.1 | 64.9 | 64.7 | 38.3 | 68.1 | 37.2 | 46.3 | 47.3 | |
| DC 245 + minors | | | | | | | | | 67 |

TABLE 6

Composition of Examples 14.1 to 14.5 (cream and soft solid compositions)

| | Example: | | | | |
|---|---|---|---|---|---|
| | 14.1 | 14.2 | 14.3 | 14.4 | 14.5 |
| C18-C36 acid glycol ester | | 2.5 | | 3.75 | |
| Castor wax | | 7.5 | | 1.25 | |
| Triacontenyl vinyl pyrrolidone copolymer | 5 | | | | |
| Paraffin wax | 5 | | | | |
| Silica | | | 1 | | 0.2 |
| Cyclopentasiloxane and cetearyl-dimethicone/vinyl dimethicone co-polymer | | | | | 64.05 |
| C12-15 alkyl benzoate | 64.3 | 63.1 | 62.9 | 63.7 | 4 |
| Dextrin palmitate | | | 10 | 5 | |
| Neopentyl glycol diheptanoate | | | | | 5 |
| PEG-8 distearate | | | | | 2 |
| Stearyl dimethicone | | | | | 0.75 |
| AACH | 25 | | | 25.5 | |
| Milled AACH | | 25.5 | 26 | | |
| AAZG | | | | | 22 |
| 4-hydroxy-3-methoxybenzyl alcohol | 0.2 | 0.4 | 0.6 | 0.8 | 1.5 |
| Perfume | 0.5 | | 0.5 | | 0.5 |

TABLE 7

Composition of Examples 15.1 to 15.8 (further cream and soft solid compositions)

| | Examples: | | | | | | | |
|---|---|---|---|---|---|---|---|---|
| | 15.1 | 15.2 | 15.3 | 15.4 | 15.5 | 15.6 | 15.7 | 15.8 |
| Silicone wax | 2.5 | | | 3 | | | | |
| N-lauroyl glutamic acid dibutylamide | | 1 | | | | | | |
| C18-C36 acid glycol ester | | | 5 | | | | | |
| C18-C36 acid triglyceride | | | 1.25 | | | | | |
| Castor wax | | | | | | | 4 | |
| Stearyl alcohol | | | | | | | 6 | |
| Paraffin wax | 7.5 | | | | | | | |
| Candelilla wax | | | | | | | | 7 |
| C24/28 alkyl dimethicone wax | | | | | | | | 3.5 |
| Silica | | | | 1.5 | 1.5 | | | |
| Talc | | 1.75 | | 6 | 5 | | | |
| Bentone 38 | | | | 3 | | | 0.5 | |
| Anhydrous aluminium silicate | | | | 6 | | | | |
| Microthene powder | | | | | 6 | | | |
| Propylene carbonate | | | | | 1.5 | | | |
| Cyclomethicone | 64.4 | 61 | 62.5 | 36.3 | 56 | 43 | | 47.8 |

TABLE 7-continued

Composition of Examples 15.1 to 15.8 (further cream and soft solid compositions)

| | Examples: | | | | | | | |
|---|---|---|---|---|---|---|---|---|
| | 15.1 | 15.2 | 15.3 | 15.4 | 15.5 | 15.6 | 15.7 | 15.8 |
| Tetraphenyl tetramethylsiloxane | | 52.7 | | | | | | |
| C12-15 Alkyl benzoate | | | | 10 | | | | 11.7 |
| Dextrin palmitate | | 5 | | | | | | 9 |
| Octyldodecanol | | 15 | | | | | | |
| PPG14 butyl ether | | | | | | 4.5 | | |
| Dimethicone (10 mPa.s) | | | 5 | | 10 | | | |
| Dimethicone (350 mPa.s) | | | | | | | 24 | |
| POE-100 stearyl ether | | | | | 2 | | | |
| POE-100 stearate | | | | | | 1 | | |
| AACH | 25.5 | | | 22 | | | | |
| Milled AACH | | 25.5 | | | | | | |
| Aluminium chlorohydrate | | | | | | | 18 | |
| AAZG | | | 25 | | 25.7 | 20 | | 26.5 |
| 4-hydroxy-3-methoxybenzyl alcohol | 0.1 | 0.3 | 0.5 | 1 | 2 | 3 | 4 | 5 |
| Perfume | | 0.5 | 0.5 | | | 0.5 | | |

TABLE 8

Composition of Examples 16.1 to 16.6 (solid stick compositions)

| | Examples: | | | | | |
|---|---|---|---|---|---|---|
| | 16.1 | 16.2 | 16.3 | 16.4 | 16.5 | 16.6 |
| Cyclomethicone (DC245) | 40.7 | 37.3 | 40.1 | 39.75 | 45.5 | |
| Permethyl 103A | 16 | 12 | | | | |
| PPG-14 Butyl ether | | | 4 | 10 | | |
| Propylene glycol | | | | | | 47.8 |
| Ethanol | | | | | | 13 |
| Isostearyl alcohol | | | | | | 12 |
| Stearyl alcohol | 14 | 14 | 17 | 11.5 | | |
| Castor wax | 2 | 5 | 2.5 | 5 | | |
| 12-hydroxystearic acid | | | | | 6 | |
| N-lauroyl glutamic acid dibutylamide | | | | | 2 | |
| Dibenzyilidene sorbitol | | | | | | 3 |
| Eicosanol | 0.2 | 0.2 | | | | |
| Octyldodecanol | | | | 14 | 14 | |
| C20-40 alcohols | | | | | 0.5 | |
| C20-40 pareth-3/C20-40 pareth-20 | | | | 1.75 | | |
| PEG-8 distearate | | | 0.6 | | 5 | |
| Amino-2-methyl-1-propanol | | | | | | 0.2 |
| ZAG | 23 | 25 | 24 | 26 | 26 | 22.5 |
| Glycerol | | | 2 | | | |
| EDTA | | | | 1 | | |
| Talc | 3 | | | | | |
| Fumed silica | | 1 | 2 | | | |
| Perfume | 1 | 1 | 1 | | | |
| 4-hydroxy-3-methoxybenzyl alcohol | 0.1 | 0.5 | 0.8 | 1 | 1 | 1.5 |

TABLE 9

Composition of Examples 17.1 to 17.6 (further solid stick compositions)

| | Examples: | | | | | |
|---|---|---|---|---|---|---|
| | 17.1 | 17.2 | 17.3 | 17.4 | 17.5 | 17.6 |
| Cyclomethicone (DC245) | 36.3 | 49.25 | 10 | 37 | | |
| Mineral oil | | 11.5 | | | | |
| Polydecene | | | 12.7 | | | |
| PPG-14 butyl ether | | | 2.5 | | | |
| C12-15 alkyl benzoate | | | | 15 | | |
| Dimethicone (50 mPa.s) | 1.5 | | | | | |
| Propylene glycol | | | | | 31 | 53.5 |
| Ethanol | | | | | 50 | |
| Water | | | | | 8.7 | 20 |
| Stearyl alcohol | 14 | | | | 1 | |
| Castor wax | 4.5 | | | | | |
| Dextrin palmitate | | 10 | | | | |
| Cellobiose octanonanoate | | | 3.8 | | | |
| Beta sitosterol | | | | 2.5 | | |
| Oryzanol | | | | 2.5 | | |
| Sodium stearate | | | | | 5.8 | 7.7 |
| Eicosanol | 0.2 | | | | | |
| Isopropyl myristate | | 10 | | | | |
| Cetyl dimethicone copolyol | | | 1 | 1 | | |
| Amino-2-methyl-1-propanol | | | | | | 0.5 |
| Poloxamer 407 | | | | | | 6 |
| Cocamide DEA | | | | | | 7 |
| Aluminium chlorohydrate | 26 | 30 | | | | |
| Zirkonal 50 | | | 51.7 | 40 | | |
| Triclosan | | | | | | 0.3 |
| Glycerol | 2 | | 17.3 | | | |
| Talc | 1.5 | | | | | |
| Fumed silica | 1 | | | | | |
| Perfume | 1 | | | | | |
| 4-hydroxy-3-methoxybenzyl alcohol | 0.5 | 0.75 | 1 | 2 | 3.5 | 5 |

The invention claimed is:
1. A cosmetic composition comprising:
 a) an antimicrobial active capable of providing sub-lethal inhibition of fatty acid catabolism by *corynebacteria A*, said antimicrobial active comprising 4-hydroxy-3-methoxybenzyl alcohol, the 4-hydroxy-3-methoxyben- zyl alcohol being present in the cosmetic composition in an amount of from 0.1 to 0.5% by weight,
b) 1 to 30% by weight of a structurant,
c) 0.1 to 10% by weight of an emulsifier, and
d) 5 to 30% by weight of an antiperspirant active wherein the composition is topically administered to the human body as a deodorant composition and wherein the cosmetic composition is in the form of a solid stick, soft solid, cream, or gel.

2. A cosmetic composition comprising:
a) an antimicrobial active capable of providing sub-lethal inhibition of fatty acid catabolism by *corynebacteria A*, said antimicrobial active comprising 4-hydroxy-3-methoxybenzyl alcohol, the 4-hydroxy-3-methoxybenzyl alcohol being present in the cosmetic composition in an amount of from 0.2 to 0.5% by weight,
b) from 10 to 98% by weight, excluding volatile propellant, of a carrier material,
c) volatile propellant selected from liquified hydrocarbons, halogenated hydrocarbon gases, alkyl ethers, and compressed non-reactive gasses, and
d) 5 to 30% by weight of an antiperspirant active, wherein the composition is topically administered to the human body as a deodorant composition and wherein the composition is in the form of an aerosol.

3. A cosmetic composition according to claim 1, wherein the 4-hydroxy-3-methoxybenzyl alcohol is present at a concentration of from 0.2 to 0.5% by weight.

4. A cosmetic composition according to claim 1 comprising an additional deodorant active.

5. A cosmetic composition according to claim 4 wherein the additional deodorant active is capable of sub-lethal inhibition of *corynebacteria A*.

6. A cosmetic composition comprising:
a) an antimicrobial active capable of providing sub-lethal inhibition of fatty acid catabolism by *corynebacteria A*, said antimicrobial active comprising 4-hydroxy-3-methoxybenzyl alcohol, the 4-hydroxy-3-methoxybenzyl alcohol being present in the cosmetic composition in an amount of from 0.1 to 0.5% by weight,
b) 1 to 30% by weight of a structurant,
c) 0.1 to 10% by weight of an emulsifier, and
d) 5 to 30% by weight of an antiperspirant active wherein the composition is topically administered to the human body as a deodorant composition and wherein the cosmetic composition is in the form of a solid stick, soft solid, cream, or gel, and wherein said composition does not comprise significant amounts of additional anti-microbial agents that cause lethal inhibition of *corynebacteria A*.

7. A cosmetic method of obtaining a deodorancy benefit comprising the topical administration of a cosmetic composition according to claim 1.

8. A cosmetic method of obtaining a deodorancy benefit comprising the topical administration of a composition according to claim 2.

9. A cosmetic composition according to claim 2 wherein the carrier material comprises a liquid polyorganosiloxane.

10. A cosmetic composition according to claim 1 which composition is non-aqueous.

11. A cosmetic composition according to claim 1, wherein the structurant is selected from the group consisting of sodium stearate, stearyl alcohol, cetyl alcohol, hydrogenerated castor oil, synthetic waxes, paraffin waxes, hydroxystearic acid, dibutyl lauroyl glutamide, alkyl silicone waxes, quaternium-18 bentonite, quaternium-18 hectorite, silica and propylene carbonate.

* * * * *